United States Patent [19]

Galtier et al.

[11] Patent Number: 5,552,410
[45] Date of Patent: Sep. 3, 1996

[54] 1,2,3,4,-TETRAHYDROQUINOLINE-8-SULPHONIC ACID CHLORIDES AND ACIDS, THEIR PREPARATION AND THEIR USE AS SYNTHETIC INTERMEDIATES

[75] Inventors: Daniel Galtier, Guyancourt; Gilbert Lassalle, Clamart, both of France

[73] Assignee: Synthelabo, Le Plessis Robinson, France

[21] Appl. No.: 305,664

[22] Filed: Sep. 14, 1994

[30] Foreign Application Priority Data

Sep. 14, 1993 [FR] France .................................. 93 10905

[51] Int. Cl.$^6$ ........................ C07D 215/36; A61K 31/47
[52] U.S. Cl. ............................. 514/311; 546/165; 546/80
[58] Field of Search ...................... 546/165, 80; 514/311

[56] References Cited

U.S. PATENT DOCUMENTS 4,617,395   10/1986   Dockner .................................. 546/178

FOREIGN PATENT DOCUMENTS 0008746   3/1980   European Pat. Off. .
0565396   10/1993   European Pat. Off. .

OTHER PUBLICATIONS

Th. E. Rawson et al., "Journal of Pharmaceutical Sciences", vol. 82, No. 6, Jun. 1993, pp. 672–673.

Primary Examiner—C. Warren Ivy
Assistant Examiner—D. Margaret M. Mach
Attorney, Agent, or Firm—Jacobson, Price, Holman & Stern, PLLC

[57] ABSTRACT

Compounds of the formula:

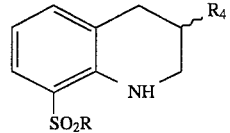

in which R represents a chlorine atom or a hydroxyl group and $R_4$ represents a $(C_1-C_4)$alkyl group in the R or S form are useful as synthetic intermediates.

9 Claims, No Drawings

1,2,3,4,-TETRAHYDROQUINOLINE-8-SULPHONIC ACID CHLORIDES AND ACIDS, THEIR PREPARATION AND THEIR USE AS SYNTHETIC INTERMEDIATES

The present invention provides optically pure derivatives of 1,2,3,4-tetrahydroquinoline-8-sulphonic acid chlorides and acids, a process for their preparation, and their use as synthetic intermediates.

The compounds of the invention are optically pure compounds of the formula:

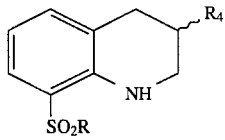
(I)

in which R represents a chlorine atom or a hydroxyl group and $R_4$ represents a $(C_1-C_4)$alkyl group in the (R) or (S) configuration.

Some compounds of formula (I), in racemic form, are described as intermediates in European Patent Application EP 0,565,396.

The compounds of the invention can be prepared by the process shown in the following Diagram 1:

Diagram 1

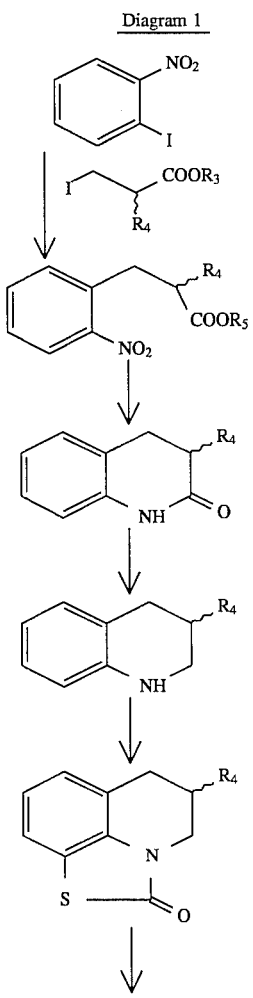

-continued
Diagram 1

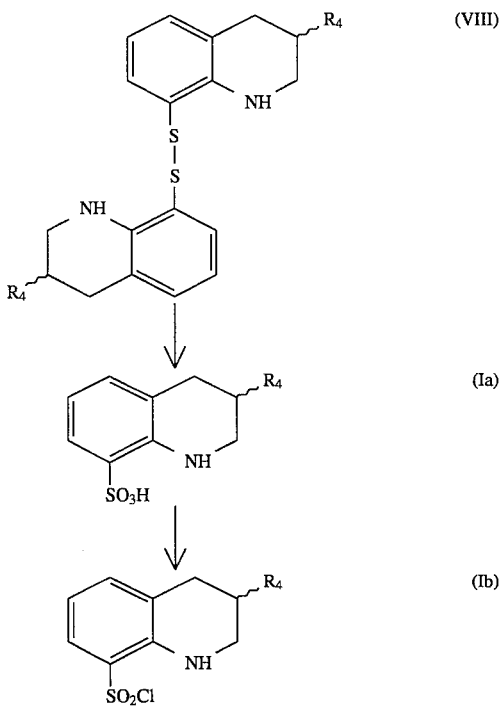

In this process an optically pure compound of formula (II) in which $R_4$ is as defined above and $R_5$ represents a $(C_1-C_4)$alkyl group in the (R) or (S) configuration, is reacted with 1-iodo-2-nitrobenzene of formula (III) in the presence of a catalyst, preferably a mixture of zinc and copper and dimethylacetamide, in an aprotic solvent such as benzene. A compound of formula (IV) is obtained which is subjected to a catalytic hydrogenation e.g. at 50 psi in the presence of a catalyst such as platinum oxide, to produce a dihydroquinoline of formula (V). The compound of formula (V) thus obtained is then reacted with borane in an aprotic solvent such as for example tetrahydrofuran to obtain a tetrahydroquinoline of formula (VI) which is reacted with chlorocarbonylsulphenyl chloride in an aprotic solvent such as for example toluene. The compound of formula (VII) obtained is treated with alcoholic potassium hydroxide and then with alumina to obtain a compound of formula (VIII). Finally, the compound of formula (VIII) is treated with hydrogen peroxide in the presence of sulphuric acid to obtain the sulphonic acid of formula (Ia).

To obtain the acid chloride of formula (Ib), the acid of formula (Ia) is reacted with sulphuryl chloride in the presence of triphenylphosphine and a base such as triethylamine in an aprotic solvent such as for example dichloromethane.

In a variant of the process, the compound of formula (V) can be prepared by reacting a compound of formula (II) with 2-iodoaniline and dimethylacetamide as catalyst and in the presence of zinc and copper in a solvent such as for example benzene.

The desired optically pure compounds are obtained using optically pure compounds of formula (II) as starting materials.

The starting materials are commercially available or are described in the literature or can be prepared by methods described therein or known to those skilled in the art. Thus, methyl R-3-iodo-2-methylpropanoate can be prepared from methyl S-3-hydroxy-2-methylpropanoate according to the method described by Nakamura et al in Tetrahedron Letters, (1987), 28, No. 3, 337–340.

The following Examples illustrate the preparation of compounds according to the invention. The microanalyses and the IR and NMR spectra confirm the structure of the compounds obtained.

EXAMPLE 1

(S)-3-methyl-1,2,3,4-tetrahydroquinoline-8-sulphonic acid 1.1. methyl (S)-α-methyl-2-nitrobenzenepropanoate 9.5 g (42 mmol) of methyl (R)-3-iodo-2-methyl propanoate are placed, under a nitrogen atmosphere and with stirring, in 90 ml of benzene containing 4.4 g of Zn(Cu) couple and 5.5 ml of dimethylacetamtde. The mixture is stirred for 15 minutes at room temperature and then heated at 60° C. for 3 hours. The mixture is then allowed to cool to room temperature and 1 g of bis(tri-O-tolylphosphine) palladium acetate in suspension in 2 ml of benzene followed by 7.5 g (30 mmol) of 1-iodo-2-nitrobenzene in solution in 20 ml of benzene are added. The mixture is heated and kept at 60° C. for 1 hour. 100 ml of ethyl acetate are added and the reaction mixture is then filtered through celite. The filtrate is washed with 100 ml of a 1N hydrochloric acid solution and then with 100 ml of water and dried over magnesium sulphate. The residue is purified by chromatography on a column of silica gel, the eluent being a hexane/ethyl acetate (90/10) mixture.

3 g of product are obtained in the form of an oil which is used as it is in the following stage.

1.2. (S)-3-methyl-3,4-dihydroquinol-2(1H)-one

Method 1

3 g (14 mmol) of the product obtained in the preceding stage are placed in 40 ml of methanol and 100 mg of platinum oxide are added. Hydrogenation is carried out under a pressure of 50 psi in a Parr apparatus for 8 hours. The mixture is filtered, the catalyst is separated and the filtrate is evaporated to dryness. The residue is recovered and triturated in ether. It is recrystallized from ethyl ether.

1.5 g of product are obtained in the form of crystals. Melting point=117°–119° C.

Method 2

31 g (135 mmol) of methyl (R)-3-iodo-2-methyl propanoate are placed, under a nitrogen atmosphere and with stirring, in 310 ml of benzene containing 19.75 g of Zn(Cu) couple and 20.3 ml of dimethylacetamide. The mixture is heated at 60° C. for 3 hours and is then cooled to room temperature. 2.92 g of bis(tri-O-tolylphosphine)palladium acetate are added in a single step and then 19.75 g (90 mmol) of 2-iodoaniline in solution in 50 ml of benzene are added. The mixture is heated for 1 hour at 50° C. and is then allowed to cool to room temperature. The mixture is filtered through celite, and the residue is washed with 2 times 100 ml of ethyl acetate. The filtrates are combined and washed successively with 2 times 100 ml of 1N hydrochloric acid solution, with 100 ml of a saturated sodium hydrogencarbonate solution, and with 50 ml of a saturated sodium chloride solution. The solution is then dried over magnesium sulphate and evaporated to dryness. The residue is purified by chromatography on a column of silica gel, eluting with dichloromethane. 4.9 g of product are obtained. Melting point=118°–120° C.

1.3. (S)-3-methyl-1,2,3,4-tetrahydroquinoline 0.8 g (5 mmol) of the compound obtained in the preceding stage is placed in 6 ml of tetrahydrofuran and 17.5 ml of a 1M solution of borane in tetrahydrofuran are added at 0° C. under a nitrogen atmosphere. The mixture is heated at reflux for 1 hour and 5 ml of water are slowly added. The pH of the reaction mixture is then adjusted to 1 with a 1N hydrochloric acid solution and the mixture is then heated under reflux for 2 hours. The mixture is allowed to cool, and is then evaporated. The residue is taken up in 50 ml of ethyl acetate and the solution is washed with 2 times 50 ml of sodium hydrogencarbonate solution, dried over magnesium sulphate and evaporated to dryness. The residue thus obtained is purified by chromatography on a column of silica gel, the eluent being dichloromethane. 0.6 g of product is obtained in the form of an oil which is used as it is in the following stage. $[\alpha]_D=+79°$ (c=3, methanol)

1.4. (S)-5-methyl-5,6-dihydro-2H,4H-thiazolo[5,4,3-ij]-quinol- 2-one 40.5 ml of toluene and then 2.28 ml (27 mmol) of chlorocarbonylsulphenyl chloride are placed under a nitrogen atmosphere with stirring. The mixture is cooled to –50° C. and then a mixture of 3.5 g (23 mmol) of the compound obtained in the preceding stage and 3.24 g (28 mmol) of N,N-dimethylbenzeneamine in solution in 130 ml of toluene is slowly added. The mixture is allowed to return to room temperature, 100 ml of toluene are added and the mixture is heated at 80° C. for 3 hours. The mixture is allowed to cool and washed with 2 times 100 ml of a 1N hydrochloric acid solution and then with 100 ml of a saturated NaCl solution. The toluene solution obtained is dried over magnesium sulphate and evaporated to dryness. The residue thus obtained is purified by chromatography on a column of silica gel, the eluent being dichloromethane. 4.3 g of product are obtained. Melting point=54°–56° C.

1.5. (S)-8,8'-dithiobis(3-methyl-1,2,3,4-tetrahydroquinoline)

1.4 g (6.8 mmol) of the compound obtained in the preceding stage are taken up in 14 ml of 3N alcoholic potassium hydroxide and heated at reflux for 6 hours. The reaction mixture is poured into 50 ml of water and the pH of the mixture is adjusted to 4–5 with hydrochloric acid. The mixture is extracted with ether, and the ether phase is collected, dried over magnesium sulphate and evaporated to dryness. The residue is taken up in 50 ml of benzene and 10 g of alumina are added. The mixture is stirred while exposed to the air for 18 hours, and the alumina is filtered off and washed is carried out with dichloromethane. The flitrates are combined and evaporated to dryness. The residue is purified by chromatography on a column of silica gel, the eluent being a cyclohexane/ethyl acetate (95/5) mixture. 0.8 g of yellow product is obtained. Melting point=78°–80° C. 1.6. (S)-3-methyl-1,2,3,4-tetrahydroquinoline-8-sulphonic acid 0.8 g (4.5 mmol) of the compound obtained in the preceding stage is dissolved in 4.51 g of a 95% sulphuric acid solution, the reaction mixture is placed in an ice bath and 1.49 ml of 35% hydrogen peroxide are slowly added. Water and then ice are subsequently added to the reaction mixture. The precipitate obtained is filtered off, washed successively with 5 ml of ice-cold water, 3 times 20 ml of ether and then 10 ml of ice-cold methanol, and finally rinsed with ether, and dried in an oven under reduced pressure. 0.5 g of product is obtained. Melting point=255° C. (decomposition) $[\alpha]_D=+38°$ C. [c=0.2, methanol/water (50/50)]

EXAMPLE 2

(S)-3-methyl-1,2,3,4-tetrahydroquinoline-8-sulphonic acid chloride 1.07 g of triphenylphosphine are dissolved in 7.5 ml of dichloromethane at 0° C. 0.3 ml of sulphuryl chloride is added dropwise under a nitrogen atmosphere at 0° C. and then the mixture is allowed to return to room temperature. A solution containing 0.47 g (2.1 mmol) of the acid obtained in the preceding stage, 0.3 ml of triethylamine and 12 ml of dichloromethane is then slowly added. Stirring is carried out for 1 hour at room temperature and the reaction mixture is then poured into 200 ml of pentane. The solution obtained is filtered. The filtrate is evaporated to dryness and the residue is taken up in 100 ml of pentane and evaporated to dryness.

0.4 g of product is obtained which is used as it is in the following stage.

EXAMPLE 3

(R)-3-methyl-1,2,3,4-tetrahydroquinoline-8-sulphonic acid (R)-3-methyl-1,2,3,4-tetrahydroquinoline-8-sulphonic acid is obtained from methyl (S)-3-iodo-2-methylpropanoate by the process described in Example 1. Melting point=255° C. (decomposition). $[\alpha]_D$=−39° C. [c=0.2, methanol/water (50/50)]

EXAMPLE 4

(R)-3-methyl-1,2,3,4-tetrahydroquinoline-8-sulphonic acid chloride (R)-3-methyl-1,2,3,4-tetrahydroquinoline-8-sulphonic acid chloride is obtained from the compound obtained in Example 3 by to the process described in Example 2.

The compounds of the invention are useful in the synthesis of compounds possessing antithrombotic activity such as those described in European Patent EP 0,008,746, for example argatroban, and the compounds of formula:

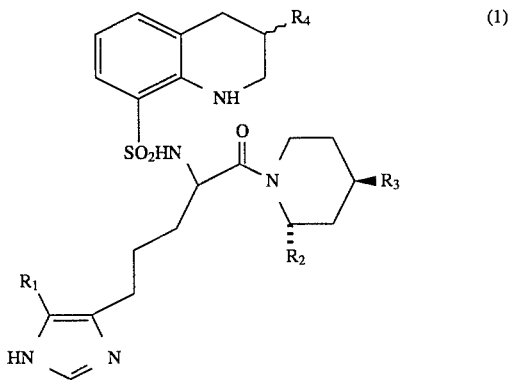

in which $R_1$ represents either a hydrogen atom or a ($C_1$–$C_4$) alkyl group, $R_2$ represents a substituent, $R_3$ represents a ($C_1$–$C_4$)alkyl group and $R_4$ is as defined above.

Compounds of formula (1) in which $R_2$ represents a hydrogen atom, a ($C_1$–$C_4$)alkoxycarbonyl group, a carboxyl group, a sodium carboxylate group, a group —$CH_2OR_4$ (where $R_4$ is a hydrogen atom, a ($C_1$–$C_4$)alkyl or ($C_1$–$C_4$)acyl group), a group —$CONR_5R_6$, or a group —$CN_4R_5$ (where $R_5$ is a hydrogen atom or a ($C_1$–$C_4$)alkyl group and $R_6$ is a hydrogen atom, a ($C_1$–$C_4$)alkyl group, a hydroxyl group, a ($C_1$–$C_4$)alkoxy group or a ($C_1$–$C_3$)alkoxyphenyl group) are described in European Patent Application EP 0,565,396.

The synthesis of the compounds of formula (1) from the compounds of the invention is shown in Diagram 2 below:

Diagram 2

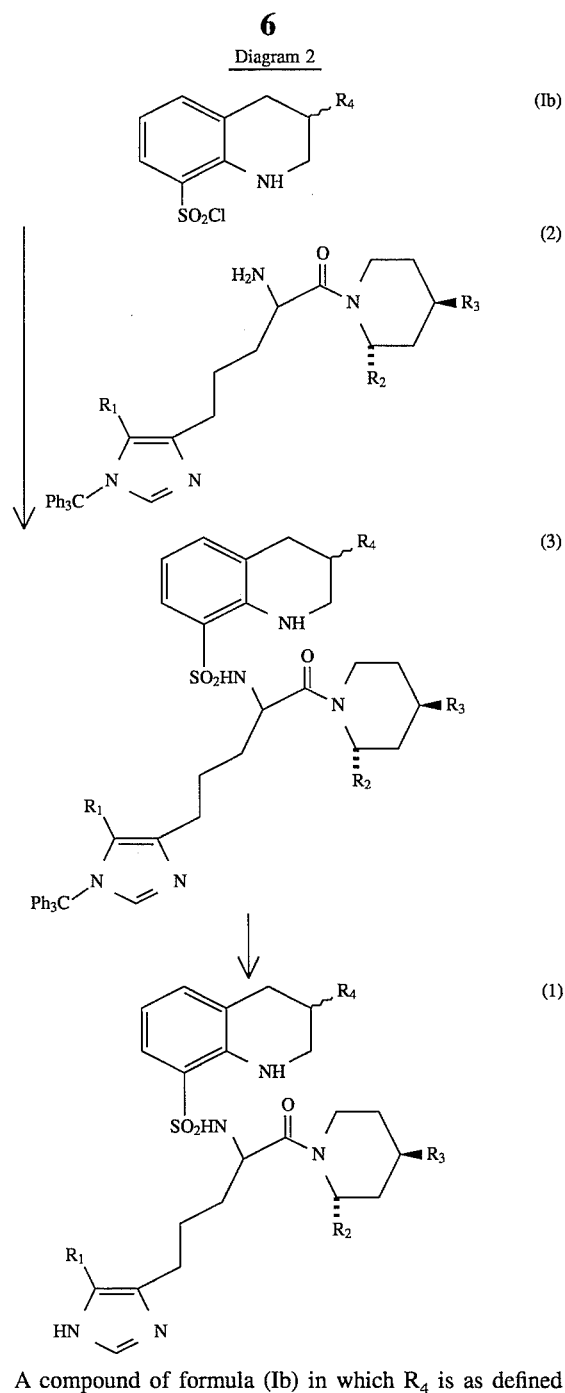

A compound of formula (Ib) in which $R_4$ is as defined above is reacted with a compound of formula (2) in which $R_1$, $R_2$ and $R_3$ are as defined above to obtain a compound of formula (3) which is deprotected while hot in the presence of acetic acid.

Example A illustrates the synthesis of compounds of formula (1) from the compounds according to the invention.

EXAMPLE A

[2R-[1(2S, 3), 2α, 4β]]-1-[5-(1H-imidazol-4-yl)-2-[[[(3-methyl-1,2,3,4-tetrahydroquinol-8yl)sulphonyl]amino]-1-oxopentyl]-4-methylpiperidine-2-methanol A.1. [2R-[1(2S, 3S), 2α, 4β]]-[4-methyl-1-[2-[[(3-methyl-1,2,3,4-tetrahydroquinol-8-yl)sulphonyl]amino]-1-oxo-5-[1-(triphenylmethyl)-1H-imidazol-4-yl]pentyl]piperid-2-yl]methyl acetate A.1.1. [2R-[1(2S), 2α, 4β]]-[1-[2-amino-1-oxo-5-[1-(triphenylmethyl)- 1H-imidazol-4-yl]pentyl]- 4-methylpiperid-2-yl]methyl acetate hydrochloride A.1.1.1. triphenyl[[1-(triphenylmethyl)-1H-imidazol-4-yl]methyl] phosphonium chloride 77.7 g (296 mmol) of triphenylphosphine are added to 670 ml of a solution of 105.5 g (294 mmol) of 4-(chloromethyl)-1-(triphenylmethyl)-1H-imidazole in dimethylformamide. The mixture is heated at 80° C. for 3 hours. The solvent is evaporated and the crude product is taken up in ether and triturated. The precipitate is filtered and dried under vacuum over phosphorus pentoxide.

162 g of product are obtained in the form of yellowish crystals. Melting point=210° C. Yield=89%

A.1.1.2. 1,1-dimethylethyl (S,E)-2-[[(phenylmethoxy)carbonyl]amino]-5-[1-(triphenylmethyl)- 1H-imidazol-4-yl] pent-4-enoate 50.93 g (820 mmol) of triphenyl[[1-(triphenylmethyl)-1H-imidazol-4-yl]methyl]phosphonium chloride in solution in 333 ml of tetrahydrofuran are introduced into a three-necked, round-bottomed flask under argon. 51.2 ml of a 1.6M solution of n-butyllithium in hexane (820 mmol) are added dropwise, at −70° C. After stirring for 30 minutes at −70° C., the reaction mixture is quickly poured into 270 ml of a 0.253M solution, cooled to −70° C., of 1,1-dimethylethyl (S)-4-oxo-2-[[(phenylmethoxy)carbonyl]amino]butanoate in tetrahydrofuran (683 mmol). The mixture is allowed to return to room temperature overnight. The mixture is hydrolysed with 280 ml of a saturated aqueous sodium chloride solution. The aqueous phase is separated from the organic phase and is extracted with 2 times 140 ml of ethyl acetate. The organic phases are combined, dried over magnesium sulphate and evaporated to dryness. Purification is carried out by chromatography on a column of silica gel, the eluent being a hexane/ethyl acetate gradient.

A mixture of cis and trans compounds is obtained. For the cis form:

Melting point=66° C.

$R_f$=0.30 [hexane/ethyl acetate (60/40)] For the trans form:

$R_f$=0.15 [hexane/ethyl acetate (60/40)

Yield=40%

A.1.1.3. (S,E)-2-[[(phenylmethoxy)carbonyl]amino]-5-[1-(triphenylmethyl)-1H-imidazol-4-yl]-pent-4-enoic acid 3.9 g (6.37 mmol) of the trans compound obtained in the preceding stage are placed in 80 ml of benzene and then a stream of gaseous hydrochloric acid is passed through at 0° C. until saturation. The mixture is stirred for 4 hours at room temperature and is then evaporated to dryness. The residue is taken up in 20 ml of dichloromethane, neutralized with ammonia and purified by chromatography on a column of silica gel, the eluent being a dichloromethane/methanol (90/10) mixture. 3 g of product are obtained. Melting point=180° C. (decomposition) p0 A.1.1.4. Phenylmethyl [2R-[1(1S), 2α, 4β]]-[1-[[2-(acetyloxy) methyl]-4-methylpiperid-1-yl] carbonyl]-4-[1-(triphenylmethyl)-1H-imidazol-4-yl]but-3-enyl]carbamate 1.67 g (3 mmol) of the compound obtained in the preceding stage, 1.5 ml of N,N-diisopropylethylamine and then 1.5 g (3.3 mmol) of benzotriazol-1-yloxytris(dimethylamino)phosphonium hexafluorophosphate are added at 0° C. to a solution of 1.14 g (3 mmol) of (2R-trans)-( 4-methylpiperid-2-yl)methyl acetate trifluoroacetate in 20 ml of dichloromethane. The mixture is left overnight at room temperature and is then poured into 100 ml of ethyl acetate. The solution obtained is washed successively with 100 ml of a 0.1N hydrochloric acid solution, 100 ml of a saturated sodium hydrogencarbonate solution and 100 ml of a saturated sodium chloride solution, dried over magnesium sulphate and evaporated to dryness. 1.4 g of product are obtained in the form of a solid. Melting point=59° C.

A.1.1.5. [2R-[1(2), 2α, 4β]]-[1-[2-amino- 1-oxo-5-[1-(triphenylmethyl)-1H-imidazol-4-yl]pentyl]- 4-methylpiperid-2-yl]methyl acetate hydrochloride 1.3 g (1.8 mmol) of the compound obtained in the preceding stage are placed in a Parr flask and 30 ml of ethanol and 0.4 g of 10% palladium-on-charcoal are added Hydrogenation is carried out at 50 psi for 8 hours. The mixture is then filtered and the catalyst sucked dry. The filtrate is collected and evaporated to dryness. The residue is taken up in 20 ml of a 0.1N solution of hydrochloric acid in isopropanol and the solution obtained is evaporated to dryness.

1.12 g of hydrochloride product are obtained. $R_f$=0.55 [methyl isobutyl ketone/acetic acid/water (60/20/20)]

A.1.2 [2R-[1(2S, 3S), 2α, 4β]]-[4-methyl-1-[2-[[(3-methyl-1,2,3,4-tetrahydroquinol-8-yl)-sulphonyl]amino]- 1-oxo-5-[1-(triphenylmethyl)-1H-imidazol- 4-yl]pentyl]piperid-2-yl]methyl acetate 0.4 g of the compound obtained in Example 2 in solution in 10 ml of dichloromethane and 0.38 ml of triethylamine in 10 ml of dichloromethane are added, at 0° C., to 0.6 g (0.9 mmol) of [2R-[1(2S), 2α,4β]]-[1-[2-amino-1-oxo-5-[1-(triphenylmethyl)-1H-imidazol-4-yl]pentyl]- 4-methylpiperid-2-yl]methyl acetate hydrochloride obtained according to the method described above. The mixture is stirred overnight at room temperature and is then washed successively with 10 ml of a 0.2N hydrochloric acid solution, 10 ml of a saturated sodium hydrogencarbonate solution and 10 ml of a saturated sodium chloride solution. The reaction mixture is filtered, dried over magnesium sulphate and evaporated to dryness. The residue is purified by chromatography on a column of silica gel, the eluent being a dichloromethane/ethanol (96/4) mixture. 0.96 g of product is obtained. Melting point=49° C.

A2. [2R-[1(2S,3S), 2α, 4β]]-[1-[5-(1H-imidazol-4-yl)-2-[[(3methyl-1,2,3,4l-tetrahydroquinol-8 -yl)-sulphonyl] amino]-1-oxopentyl]-4-methylpiperid-2-yl-methyl acetate 0.65 g (0.74 mmol) of the compound obtained in the preceding stage is placed in 10 ml of acetic acid. 2 ml of water and 8 ml of tetrahydrofuran are added and the mixture is then heated at 80° C. for 1 hour. The reaction mixture is evaporated to dryness and the residue is purified by chromatography on a column of silica gel, the eluent being a dichloromethane/ethanol (90/10) mixture. 0.4 g of pure product is obtained. Melting point=47° C. A.3. [2R-[1(2S, 3S), 2α, 4β]]-1-[5-(1H-imidazol-4-yl)-2-[[(3-methyl-1,2,3, 4-tetrahydroquinol- 8-yl)-sulphonyl]amino]-1-oxopentyl]-4-methylpiperidine-2-methanol 0.4 g (0.75 mmol) of the compound obtained in the preceding stage is placed in 2 ml of methanol, cooled to 0° C. and 1.5 ml of a 1N sodium hydroxide solution are added dropwise. The mixture is left stirring for 2 hours at 0° C., the methanol is evaporated and the residue is suspended in a dichloromethane/water (50/50) mixture. The organic phase is recovered and is dried over magnesium sulphate and evaporated to dryness. The residue is taken up in one equivalent of a 1N hydrochloric acid solution and is purified by chromatography on a column of silica gel, the eluent being a 0.01N hydrochloric acid and acetonitrile gradient (0 to 100% in acetonitrile). The fractions containing the product are combined and lyophilized. 0.3 g of product is obtained. Melting point=90° C. $[α]_D$=+110° (c=0.2, methanol).

We claim:
1. An optically pure compound of the formula:

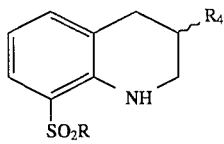

in which R represents a chlorine atom or a hydroxyl group and $R_4$ represents a $(C_1-C_4)$alkyl group.

2. A compound according to claim 1, which is (S)-3-methyl-1,2,3,4-tetrahydroquinoline-8-sulphonic acid.

3. A compound according to claim 1, which is (S)-3-methyl-1,2,3,4-tetrahydroquinoline-8-sulphonic acid chloride.

4. A compound according to claim 1, which is (R)-3-methyl-1,2,3,4-tetrahydroquinoline-8-sulphonic acid.

5. A compound according to claim 1, which is (R)-3-methyl-1,2,3,4-tetrahydroquinoline-8-sulphonic acid chloride.

6. Process for the preparation of compound according to claim 1, which comprises reacting an optically pure compound of formula:

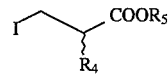

in which $R_4$ is as defined in claim 10 and $R_5$ represents a $(C_1-C_4)$ alkyl group, with 1-iodo-2-nitrobenzene in the presence of a catalyst in an aprotic solvent, subjecting the compound obtained of formula:

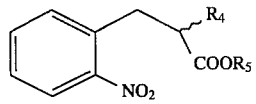

to catalytic hydrogenation to obtain a dihydroquinoline of formula:

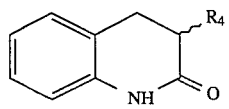

reacting the compound of formula V obtained with borane in an aprotic solvent to produce a tetrahydroquinoline of formula:

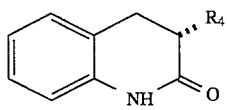

reacting the compound of formula VI with chlorocarbonylsulphenyl chloride in an aprotic solvent to produce a compound of formula:

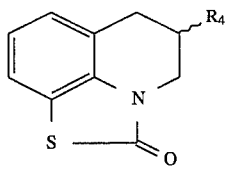

reacting the compound of formula VII with alcoholic potassium hydroxide and then with alumina to produce a compound of formula:

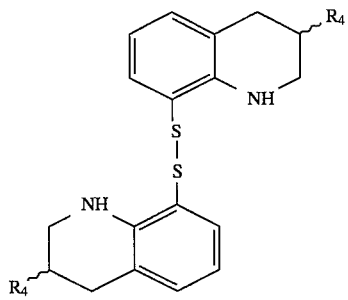

treating the compound of formula VIII with hydrogen peroxide in the presence of sulphuric acid to produce a sulphonic acid of formula I wherein R represents a hydroxyl group, and optionally converting the said acid into its acid chloride by reaction with sulphenyl chloride in the presence of triphenylphosphine and a base in an aprotic solvent to produce a compound of formula I wherein R represents a chlorine atom.

7. Process according to claim 6, wherein the starting material of formula (II) is methyl R-3-iodo-2-methylpropanoate.

8. Process according to claim 6, wherein the starting material of formula (II) is methyl S-3-iodo-2-methylpropanoate.

9. A method of using the compound according to claim 1, for the preparation of compounds possessing antithrombotic activity.

* * * * *